(12) United States Patent
Neliat

(10) Patent No.: US 12,208,079 B2
(45) Date of Patent: Jan. 28, 2025

(54) ENANTIOMERS OF A2-73, ANALOGUES, AND SIGMA AGONIST ACTIVITY

(71) Applicant: Anavex Life Sciences Corp., New York, NY (US)

(72) Inventor: Gervais Neliat, Le Bois l'Eveque (FR)

(73) Assignee: Anavex Life Sciences Corp., New York, NY (US)

( * ) Notice: Subject to any disclaimer, the term of this patent is extended or adjusted under 35 U.S.C. 154(b) by 0 days.

(21) Appl. No.: 17/959,920

(22) Filed: Oct. 4, 2022

(65) Prior Publication Data

US 2023/0044710 A1    Feb. 9, 2023

Related U.S. Application Data

(62) Division of application No. 15/579,696, filed as application No. PCT/IB2016/001158 on Jul. 19, 2016, now Pat. No. 11,617,734.

(60) Provisional application No. 62/195,417, filed on Jul. 22, 2015.

(51) Int. Cl.
| | | |
|---|---|---|
| *A61K 31/341* | (2006.01) | |
| *A61P 9/10* | (2006.01) | |
| *A61P 25/00* | (2006.01) | |
| *A61P 25/28* | (2006.01) | |
| *A61P 39/00* | (2006.01) | |
| *C07D 231/22* | (2006.01) | |
| *G01N 33/50* | (2006.01) | |

(52) U.S. Cl.
CPC ............ *A61K 31/341* (2013.01); *A61P 25/28* (2018.01); *C07D 231/22* (2013.01); *G01N 33/5005* (2013.01)

(58) Field of Classification Search
CPC ..... A61K 31/341; A61K 9/0053; A61P 25/28; A61P 25/00; A61P 9/10; A61P 39/00; C07D 231/22; G01N 33/5005
See application file for complete search history.

(56) References Cited

FOREIGN PATENT DOCUMENTS

| | | |
|---|---|---|
| FR | 2983732 B1 | 11/2013 |
| GR | 1008233 B | 6/2014 |
| JP | 2013121956 A | 6/2013 |
| JP | 2014529613 A | 11/2014 |
| WO | 9730983 A1 | 8/1997 |
| WO | WO-2013008044 A1 * | 1/2013 |
| WO | 2013029060 A2 | 2/2013 |
| WO | 2014155138 A1 | 10/2014 |

OTHER PUBLICATIONS

ANAVEX., "Therapeutic Candidates," 2022, Retrieved from Internet URL: https://www.anavex.com/therapeutic-candidates, 5 pages.

Collina S., et al., "Sigma Receptor Modulators: A Patent Review," Expert Opinion on Therapeutic Patents, Feb. 7, 2013, vol. 23(5), XP055538759, pp. 597-613.

Extended European Search Report issued in European Application No. 16827322.5, mailed on Jan. 23, 2019, 8 pages.

(Gyo-ke) No. 10170 Decision (case of appeal against decision), rendition of judgement on Aug. 7, 2014, 26 pages.

International Preliminary Report on Patentability for International Application No. PCT/IB2016/001158 mailed Feb. 1, 2018, 9 pages.

International Search Report and Written Opinion for International Application No. PCT/IB2016/001158 mailed Dec. 5, 2016, 14 pages.

Lahmy V., et al., "Blockade of Tau Hyperphosphorylation and a beta 1-42 Generation by the Aminotetrahydrofuran Derivative ANAVEX2-73, A Mixed Muscarinic and Gammal Receptor Agonist, in a Nontransgenic Mouse Model of Alzheimer's Disease," Neurophychopharmacology, Aug. 2013, vol. 38(9), pp. 1706-1723.

Lahmy V., et al., "Mitochondrial Protection by the Mixed Muscarininc /[sigma]1 Ligand Anavex 2-73, a Tetrahydrofuran Derivative, in A[beta]25-35 Peptide-injected Mice, A Nontransgenic Alzheimer's Disease Model," Frontiers in Cellular Neuroscience, Jan. 20, 2015, vol. 8, Article 463, 11 Pages.

MacFarlane S., et al., "New Exploratory Alzheimer's Drug Anavex 2-73 changes in Electrophysiological Markers in Alzheimer's Disease: First Patient data from an ongoing Phase 2a study in mild-to-moderate Alzheimer's Patients," Alzheimer's Dementia, The Journal of the Alzheimer's Association, vol. 11(7), 1 Page, XP029355199, ISSN: 1552-5260, DOI: 10.1 016/J.JALZ.2015.08.130.

Nakazawa M., et al., "Activation of Sigma1 Receptor Subtype Leads to Neuroprotection in the Rat Primary Neuronal Cultures," Neurochemistry International, Apr. 1998, Retrieved from Internet URL: https://pubmed.ncbi.nlm.nih.gov/9596556/, vol. 32, No. 04, pp. 337-343.

Nguyen L.A., et al., "Chiral Drugs: An Overview," International Journal of Biomedical Science, 2006, vol. 2(2), pp. 85-100.

Office Action for Japanese Application No. 2017-564725, mailed on Dec. 27, 2022, 11 pages.

Office Action for Japanese Application No. 2021-110038, mailed on Feb. 27, 2023, 4 pages.

Reagan-Shaw S., et al., "Dose Translation from Animal to Human Studies Revisited," The FASEB Journal, 2007, vol. 22, pp. 659-661.

(Continued)

*Primary Examiner* — Sun Jae Yoo
(74) *Attorney, Agent, or Firm* — POLSINELLI PC

(57) ABSTRACT

A pharmaceutical preparation comprising ⊖A2-73 substantially free of ⊕ A2-73. This invention further includes a method treating Alzeheimer's disease in a subject in need of such treatment by the method of administering a therapeutically effective amount of ⊖A2-73 substantially free of ⊕ A2-73.

This invention yet further includes a method of classifying cells as to sigma receptor type by the method of exposing said cells to a detectable amount of ⊖A2-73 substantially free of ⊕ A2-73 and determining the level of sigma receptor binding.

4 Claims, No Drawings

(56) References Cited

OTHER PUBLICATIONS

Sanchez-Blazquez P., et al., "The Sigma-1 Receptor Antagonist, S1RA, Reduces Stroke Damage, Ameliorates Post-Stroke Neurological Deficits and Suppresses the Overexpression of MMP-9," Molecular Neurobiology, Jun. 2018, Retrieved from Internet URL: https://pubmed.ncbi.nlm.nih.gov/28779350/, vol. 55, No. 06, pp. 4940-4951.

Schetz J.A., et al., "A Prototypical Sigma-1 Receptor Antagonist Protects Against Brain Ischemia," Brain Research, Nov. 21, 2007, Retrieved from Internet URL: https://pubmed.ncbi.nlm.nih.gov/17919467/, vol. 1181, pp. 1-9.

Szokol Z., et al., "Assignment of Absolute Configuration to Enantiomers of Anti-Alzheimer Drug Candidate Blarcamesine," Periodica Polytechnica Chemical Engineering, 2022, vol. 66, No. 4, pp. 536-540.

Takashi Tsuji, "Chirality in Our Life," Chemistry and Education, 1995, vol. 43, No. 11, pp. 691-694.

Villard V., et al., "Anti-Amnesic and Neuroprotective Potentials of the Mixed Muscarinic Receptor/Sigma1 Ligand ANAVAEX2-73, a Novel Aminotetrahydrofuran Derivative," Journal of Psychopharmacology, Aug. 2011, vol. 25, No. 3, pp. 1101-1117.

Yasushi Yamazoe, Kiyoshi Nagata, Farumashia, 1989, vol. 25, No. 4, pp. 333-336.

Leonard B.E., "An Introduction to Enantiomers in Psychopharmacology," Human Psychopharmacology: Clinical and Experimental, 2001, vol. 16, pp. S79-S84.

Office Action for Canadian Application No. 2,986,345 mailed on Aug. 16, 2023, 6 pages.

Office Action for Japanese Patent Application No. 2023-051980, mailed on Mar. 11, 2024, 14 pages.

Office Action for Japanese Patent Application No. 2023-051980, mailed on Jul. 24, 2024, 8 pages.

European Medicines Agency, "Investigation of Chiral Active Substances," Oct. 1993, pp. 381-391, Retrieved from the Internet: URL: https://www.ema.europa.eu/en/investigation-chiral-active-substances-human-scientific-guideline.

Food and Drug Administration (USA), "Development of New Stereoisomeric Drugs," May 1, 1992, 7 pages, Retrieved from the Internet: URL: https://www.fda.gov/regulatory-information/search-fda-guidance-documents/development-new-stereoisom-eric-drugs.

Office Action for Canadian Application No. 2,986,345 mailed on Sep. 3, 2024, 7 pages.

* cited by examiner

ENANTIOMERS OF A2-73, ANALOGUES, AND SIGMA AGONIST ACTIVITY

CROSS REFERENCE TO RELATED APPLICATIONS

This application is a divisional application of and claims the benefit of U.S. Patent Applications with the Ser. No. 15/579,696, filed Dec. 5, 2017, which is a national stage application under 35 U.S.C. § 371 of the International Application Number PCT/IB2016/001158, filed Jul. 19, 2016, which claims the priority from Provisional Application No. 62/195,417, filed Jul. 22, 2015, the contents of each are hereby incorporated by reference in their entireties.

FIELD OF THE INVENTION

A pharmaceutical preparation comprising ⊖A2-73 substantially free of ⊕ A2-73. This invention further includes a method treating Alzheimer's disease in a subject in need of such treatment by the method of administering a therapeutically effective amount of ⊖A2-73 substantially free of ⊕ A2-73.

This invention yet further includes a method of classifying cells as to sigma receptor type by the method of exposing said cells to a detectable amount of ⊖A2-73 substantially free of ⊕ A2-73 and determining the level of sigma receptor binding.

BACKGROUND OF THE INVENTION

Two sigma receptor subtypes have been identified based on their pharmacological profile. The sigma-1 (σ-1) receptor has been cloned (Hanner et al., 1996). The sigma-2 receptor has been reported as a separate molecular entity (Langa et al., 2003). The sigma-1 receptor has been reported as having high affinity for positive isomer of bezomorphas such as (+)-pentazocine and (+)-SKF-10,047. The sigma-2 receptor has been reported as having a high affinity for ibogaine (Vilner and Bowen, 2000). In particular, sigma 1 receptor agonists have also been has been reported as having antidepressant effects. In this regard, Sigma 1 receptor ligands show clear antidepressant effects in several animal models. By way of example, the selective sigma 1 receptor agonists (+)-pentazocine, (+)-SKF-10,047, igmesine, OPC14523, DTG or SA4503 reduce the immobility time in the forced swim test or are active in the tail suspension test (Ukai et al. 1998, Matsuno et al., 1996, Tottori et al. 1997, Kinsora et al. 1998). U.S. Pat. No. 5,034,419 describes N-cycloalkylalkylamines, which is also reportedly a sigma 1 receptor agonist.

The sigma-1 receptor, first reported cloned in 1996, is a single polypeptide transmembrane protein comprising 223 amino acids. It is mainly located on the endoplasmic reticulum membrane. The sigma-1 receptor is reported to be expressed in ocular tissues including the cornea, lens and retina. It has also been reported to play a role in cell survival (Wang et al., Exp Cell Research, Vol. 312(8):1439-1446, 2006); Hayashi et al., Cell, Vol. 131(3):596-610, November 2007; Jiang et al., IOVS, Vol. 47(12):5576-5582, 2006).

Sigma receptor ligands have been reported to be neuroprotective. The sigma receptor ligand opipramol was reported as protected against ischemia in gerbils. In addition, other sigma ligands, including BMY-14802, caramiphen and haloperidol, exhibited properties in in vivo models that are consistent with protective effects (Pontecorvo et al., Brain Research Bulletin, Vol. 26:461-465, 1991). Several sigma ligands were reported to inhibit ischemia-induced glutamate release from hippocampal slice preparations in vitro (Lobner et al., Neuroscience Letters, Vol. 117:169-174, 1990). It has also been reported that the Sigma-1 receptor agonist (+)-pentazocine can protect the retinal cells against stress (Dun et al., IOVS, Vol. 48(10):4785-4794, 2007; Smith et al., IOVS, Vol. 49(9):4154-4161, 2008).

Iñiguez et al., has reported that treatment of Jurkat T cells with sigma-2 (σ-2) agonists decreased the induction of the expression of Interleukin (IL)-2, Tumor necrosis factor (TNF)-α, and Cyclooxygenase (COX)-2 by activated T cells in a dose-dependent manner. ("Inhibitory effects of sigma-2 receptor agonists on T lymphocyte activation," *Front. Pharmacol* 13 Mar. 2013|doi: 10.3389/fphar.2013.00023.) Reported effects take place at the transcriptional level since σ-2 agonists BD-737 and CB-184 diminished the activity of the promoters of those genes. Those immunosuppressive effects could be attributable to interference with transcription factor activation. Induced transcription mediated by Nuclear factor (NF)-κB or Nuclear Factor of Activated T cells (NFAT) was inhibited by σ-2 agonists. The authors suggested that these effects were specific for σ-2 agonists as no significant effects on T cell activation by σ-1 ligands PRE-084 [2-(4-Morpholinethyl)1 Phenylcyclohexanecarboxylate] and BD-1063 were found. By way of non-limiting example, reported σ-2 agonists include CB-64D, CB-184, BD-737, and haloperidol.

A receptor antagonist is a type of receptor ligand or drug that blocks or dampens agonist-mediated responses rather than provoking a biological response itself upon binding to a receptor. In pharmacology, antagonists have affinity but no efficacy for their cognate receptors, and binding will disrupt the interaction and inhibit the function of an agonist or inverse agonist at receptors. Antagonists mediate their effects by binding to the active (orthosteric=right place) site or to allosteric (=other place) sites on receptors, or they may interact at unique binding sites not normally involved in the biological regulation of the receptor's activity. Antagonist activity may be reversible or irreversible depending on the longevity of the antagonist-receptor complex, which, in turn, depends on the nature of antagonist-receptor binding. The majority of drug antagonists achieve their potency by competing with endogenous ligands or substrates at structurally defined binding sites on receptor.

Competitive as to an agonist or antagonists (also known as surmountable) reversibly binds the agonist or antagonist to receptors at the same binding site (active site) as the endogenous ligand or agonist/antagonist, but without activating the receptor. Agonists and antagonists "compete" for the same binding site on the receptor. Once bound, an antagonist will block the opposite functioning molecule from binding. The level of activity of the receptor will be determined by the relative affinity of each molecule for the site and their relative concentrations. High concentrations of a competitive agonist or antagonist will increase the proportion of receptors that the that molecule occupies, higher concentrations of the molecule will be required to obtain the same degree of binding site occupancy. In functional assays using competitive antagonists, a parallel rightward shifts of agonist dose-response curves with no alteration of the maximal response is observed.

The term "non-competitive" (sometimes called non-surmountable antagonists) can be used to describe two distinct phenomena: one in which the agonist or antagonist binds to the active site of the receptor, and one in which the agonist/antagonist binds to an allosteric site of the receptor. While the mechanisms are different in both of these phenomena, they are both called "non-competitive" because the end-results of each are functionally very similar. Unlike competitive, which affects the amount of agonist or antagonist necessary to achieve a maximal response but do not affect the magnitude of that maximal response, non-competitive agonist or antagonists reduce the magnitude of the maximum response that can be attained by any amount of agonist or antagonist. http://en.wikipedia.org/wiki/Receptor_antagonist-cite_note-Vauquelin2002-19

Sigma1—Without being bound by any particular theory it is believed that Sigma1 receptors regulate neurotransmission via the NMDA receptor and the release of neurotransmitters such as dopamine and acetylcholine. It is thus proposed that the sigma1 receptors play a role in learning and memory as well as in certain neuropsychiatric disorders.

Antagonists—Sigma1 antagonists are believed useful in treating schizophrenic associated symptoms of blunted affect, anhedonia, avolition or apathy, and alogia. Sigma1 antagonists are also believed useful in attenuating orofacial dyskinesias and dystonic reactions associated as side-effects of physochotropic drugs. Sigma1 antagonists are also believed useful as cancer anti-proliferatives.

Agonists—Sigma1 agonists are useful as antidepressants. Particular note is made of the utility of a Sigma1 agonist with low Sigma2 affinity in treating ischemic brain/neuronal injury such as from focal ischemia. Sigma1 agonists are also believed useful in improving cognitive impairment such as exhibited with impaired neurotransmitter function (e.g., acetylcholine) as well as age associated cognitive impairment, and anxiety associated impairment (including pregnancy stress resulting in learning deficits of offspring).

Sigma2—Sigma2 receptors are believed useful as a target for motor function and cancer treatment. Sigma2 receptors are expressed in high densities in rapidly proliferating cancer cells.

Antagonists—Sigma2 antagonists are useful in the treatment of irreversible motor side effects such as those reported after the long-term administration of typical antipsychotic drugs.

Reference is made to *Sigma Receptors: Chemistry. Cell Biology and Clinical Implications*, Eds Matsumoto et al., Springer; 2007 edition (Nov. 16, 2014). The teaching of this publication and all references cited herein are incorporated by reference in their entirety. Additional reference is made to:

Nguyen et al, "Role of sigma-1 receptors in neurodegenerative diseases," *J Pharmacol Sci.* 2015 January; 127(1): 17-29;

Guo et al., Sigma-2 receptor ligands: neurobiological effects," *Curr Med Chem.* 2015; 22(8):989-1003;

U.S. Ser. No. 62/065,833 entitled "A19-144, A2-73 and Certain Anticholinesterase Inhibitor Compositions and Method for Anti-Seizure Therapy," filed Oct. 20, 2014;

Crawford et al., "Sigma-2 Receptor Agonists Activate a Novel Apoptotic Pathway and Potentiate Antineoplastic Drugs in Breast Tumor Cell Lines," *Cancer Research*, 62, 313-322, Jan. 1, 2002;

Rossi et al., "A step forward in the sigma enigma: a role for chirality in the sigma1 receptor-ligand interaction?" *Medicinal Chemistry Communication* (Impact Factor: 2.63). September 2014; 6(1);

U.S. Pub. No. 20110206780 entitled "Morphinan modulators of nmda receptors, sigma1 receptors, sigma2 receptors, and/or a3b4 nicotinic receptors," to Gant et al., having a priority date of Jan. 6, 2010.

WO2013008044 to Vamvakides et al. entitled "SYNTHESIS OF (+) AND (−) 1-(5,5-DIPHENYLTETRAHYDRO-FURAN-3-YL)-N,N-DIMETHYLMETHANAMINE, (+) AND (−) 1-(2,2-DIPHENYLTETRAHYDROFURAN-3-YL)-N,N-DIMETHYLMETHANAMINE AND (+) AND (−) 1-(2,2-DFFHENYLTETRAHYDROFURAN-3-YL)-N-METIHYLMETHANAMINE" sets fort chiral separatory methodology.

U.S. Patent application entitled "ANAVEX2-73 FOR THE TREATMENT OF ALZHEIMER'S DISEASE" and filed on date even herewith.

U.S. Patent Application entitled "CRYSTAL FORMS OF tetrahydro-N,N-dimethyl-2,2-diphenyl-3-furanmethanamine hydrochloride, PROCESSES OF MAKING SUCH FORMS, AND THEIR PHARMACEUTICAL COMPOSITIONS" and filed on date even herewith.

SUMMARY OF THE INVENTION

A pharmaceutical preparation comprising ⊖A2-73 substantially free of ⊕ A2-73.

This invention further includes a method of therapeutic treatment of a subject in need of enhanced stimulation of sigma 1 receptors by administering a therapeutically effective dose of pharmaceutical preparation comprising ⊖A2-73 substantially free of ⊕ A2-73. Particularly noted is the pharmaceutical preparation of ⊖A2-73 substantially free of ⊕ A2-73 of from about 0.5 to about 100 mg ⊖A2-73 and particularly 1-20 mg.

A method of treating Alzeheimer's disease in a subject in need of such treatment by the method of administering a therapeutically effective amount of ⊖A2-73 substantially free of ⊕ A2-73.

Further noted is a method of classifying cells as to sigma receptor type by the method of exposing said cells to a detectable amount of ⊖A2-73 substantially free of ⊕ A2-73 and determining the level of sigma receptor binding

DETAILED DESCRIPTION OF THE INVENTION

This invention will be better understood with reference to the following definitions:

A. ANAVEX2-73, or A2-73 shall mean tetrahydro-N,N-dimethyl-2,2-diphenyl-3-furanmethanamine hydrochloride. This is listed in some of the test data as AE 37. A2-73 is a compound which is believed to bind to muscarinic acetylcholine and sigma-1 receptors with affinities in the low micromolar range.

B. ANAVEX19-144 or A19-144 shall mean 1-(2,2-diphenyltetrahydrofuran-3-yl)-N-methylmethanamine hydrochloride. A19-144 is a compound which is believed to bind to muscarinic acetylcholine and sigma-1 receptors with affinities in the low micromolar range.

C. ANAVEX1-41 or A1-41 shall mean tetrahydro-N,N-dimethyl-5,5-diphenyl-3-furanmethanamine hydrochloride. This is listed in some of the test data as AE 14. A1-41 is reported in Villard et al., "Antiamnesic and Neuroprotective Effects of the Aminotetrahydrofuran Derivative ANAVEX1-41 Against Amyloid b25-35-Induced Toxicity in Mice," *Neuropsychopharmacology*, 1-15 (2008).

D. The term "enantiomer" or "enantiomeric" refers to a molecule that is nonsuperimposeable on its minor image and hence optically active wherein the enantiomer rotates the plane of polarized light in one direction and its minor image rotates the plane of polarized light in the opposite direction.

E. "Substantially free" as to defining enantiomers ⊕ form absent ⊖ form or ⊖ form absent ⊕ form shall mean less than about 2% (w/w) of the excluded form and preferably less than about 1% and more preferably less than about 0.5%, and in some cases less than about 0.1%.

F. "Classifying" cells as to the σ 1 or 2 receptor populations shall mean determining the presence and or density of either a 1 or 2 receptors on cell surfaces in a given cell population. Classifying takes advantage of the differential populations of sigma receptors used as biomarkers. Biomarkers are useful as a means to define cell population propensities such as the likelihood of proliferation as to breast cancers. Testing methodology is more fully set forth in the following:

Hashimoto et al., "Sigma receptor ligands: possible application as therapeutic drugs and as radiopharmaceuticals," Curr Pharm Des. 2006; 12(30):3857-76;

Mach R H et al., "Sigma 2 receptors as potential biomarkers of proliferation in breast cancer," Cancer Res 1997; 57: 156-61;

Al-Nabulsi, I et al., "Effect of ploidy, recruitment, environmental factors, and tamoxifen treatment on the expression of sigma-2 receptors in proliferating and quiescent tumour cells," Br J Cancer 1999; 81: 925-33; and, Wheeler K T et al., "Sigma-2 receptors as a biomarker of proliferation in solid tumours," Br J Cancer 2000; 82: 1223-32.

A2-73⊖ is a selective noncompetitive agonist for σ1 receptors and a significantly stronger agonist than A2-73⊕.

The pharmacologically active compositions of this invention can be processed in accordance with conventional methods of Galenic pharmacy to produce medicinal agents for administration to subjects, e.g., mammals including humans.

Studies were conducted to on the effects of several compounds in various in vitro receptor binding and isolated organ assays.

1. Materials and Methods 1.1. In Vitro Pharmacology: Binding Assays
1.1.1. General Procedures

| Assay | Origin | Reference Compound | Bibliography |
| --- | --- | --- | --- |
| σ$_1$ (h) | Jurkat cells | haloperidol | Ganapathy et al. (1999) |
| σ$_2$ | rat cerebral cortex | haloperidol | Bowen et al. (1993) |

1.1.2. Experimental Conditions

| Assay | Ligand | Conc. | Non Specific | Incubation | Method of Detection |
| --- | --- | --- | --- | --- | --- |
| σ$_1$ (h) | [$^3$H](+) pentazocine | 8 nM | haloperidol (10 μM) | 120 min./ 22° C. | Scintillation counting |
| σ$_2$ | [$^3$H]DTG (+ 300 nM (+)pentazocine) | 5 nM | haloperidol (10 μM) | 120 min./ 22° C. | Scintillation counting |

As a general statement, in vitro results showing an inhibition (or stimulation for assays run in basal conditions) higher than 50% are considered to represent significant effects of the test compounds. 50% is the most common cut-off value for further investigation (determination of IC$_{50}$ or EC$_{50}$ values from concentration-response curves).

Results showing an inhibition (or stimulation) between 20% and 50% are indicative of weak to moderate effects (in some assays, they may be confirmed by further testing as they are within a range where more inter-experimental variability can occur).

Results showing an inhibition (or stimulation) lower than 20% are not considered significant and mostly attributable to variability of the signal around the control level.

Low to moderate negative values have no real meaning and are attributable to variability of the signal around the control level. High negative values (>50%) that are sometimes obtained with high concentrations of test compounds are generally attributable to non-specific effects of the test compounds in the assays.

1.1.3. Analysis and Expression of Results

The specific ligand binding to the receptors is defined as the difference between the total binding and the nonspecific binding determined in the presence of an excess of unlabelled ligand.

The results are expressed as a percent of control specific binding and as a percent inhibition of control specific binding obtained in the presence of the test compounds. Individual and mean values are presented in the results section.

The IC$_{50}$ values (concentration causing a half-maximal inhibition of control specific binding) and Hill coefficients (n$_H$) were determined by non-linear regression analysis of the competition curves using Hill equation curve fitting. The inhibition constants (K$_i$) were calculated from the Cheng Prusoff equation (K$_i$=IC$_{50}$/(1+(L/K$_D$)), where L=concentration of radioligand in the assay, and K$_D$=affinity of the radioligand for the receptor).

1.2. In Vitro Pharmacology: Isolated Organ Bioassay
1.2.1. General Procedures

| Assay | Tissue | Reference agonist | Response | Reference antagonist | Bibliography |
| --- | --- | --- | --- | --- | --- |
| M$_1$ | rabbit vas deferens (field-stimulated) | McN-A-343 | inhibition of twitch contraction | pirenzepine | Eltze (1988) |

1.2.2. Experimental Conditions

Prostatic segments of rabbit vas deferens were suspended in 20-ml organ baths containing an oxygenated (95% O$_2$ and 5% CO$_2$) and pre-warmed (30° C.) physiological salt solution of the following composition (in mM): NaCl 118.0, KCl 4.7, MgSO$_4$ 0.6, CaCl$_2$) 2.5, KH$_2$PO$_4$ 1.2, NaHCO$_3$ 25 and glucose 11.0 (pH 7.4).

Yohimbine (1 μM) and naloxone (1 μM) were also present throughout the experiments to block the α$_2$-adrenergic and opioid receptors, respectively.

The tissues were connected to force transducers for isometric tension recordings. They were stretched to a resting tension of 1 g then allowed to equilibrate for 60 min during which time they were washed repeatedly and the tension readjusted. Thereafter, they were stimulated electrically with square wave pulses (submaximal intensity, 1 msec duration, 0.1 Hz) delivered by a constant current stimulator.

The experiments were carried out using a semi-automated isolated organ system possessing eight organ baths, with multichannel data acquisition.

1.2.3. Experimental Protocols

Test for Agonist Activity

The tissues were exposed to a submaximal concentration of the reference agonist McN-A-343 (1 μM) to verify responsiveness and to obtain a control response. Following washings and recovery of the initial twitch contractions, the tissues were exposed to the test compounds or the same agonist which were left in contact with the tissues until a stable response was obtained or for a maximum of 15 min.

If an agonist-like response (inhibition of twitch contractions) was obtained, the reference antagonist pirenzepine (0.1 μM) was tested against the test compounds to confirm the involvement of the $M_1$ receptors in this response.

Test for Antagonist Activity

The tissues were exposed to a submaximal concentration of the reference agonist McN-A-343 (1 μM) to obtain a control response.

After stabilization of the McN-A-343-induced response, the tissues were exposed to the test compounds or the reference antagonist pirenzepine which were left in contact with the tissues until a stable response was obtained or for a maximum of 15 min. If it occurred, a recovery of the twitch contraction amplitude by the test compounds indicated an antagonist activity at the $M_1$ receptors.

1.2.4. Analysis and Expression of Results

The parameter measured was the maximum change in the amplitude of the electrically-evoked contractions induced by the compounds.

The results are expressed as a percent of the control response to McN-A-343 (mean values).

Compounds

1.3. Test Compounds

From: EURO GENET Lab A.E.

| CEREP I.D. | Compound I.D. | Reference Number | Submitted F.W. | Stock Solution | Intermediate Dilution |
|---|---|---|---|---|---|
| 9327-1 | (+) A1-41 | | 318.00 | 1.E−02M DMSO | 1.E−04M H2O |
| | | | | 1.E−02M DMSO | Direct addition * |
| 9327-2 | (−) A1-41 | | 318.00 | 1.E−02M DMSO | 1.E−04M H2O |
| | | | | 1.E−02M DMSO | Direct addition * |
| 9327-3 | (+) A2-73 | | 318.00 | 1.E−02M DMSO | 1.E−04M H2O |
| 9327-4 | (−) A2-73 | | 318.00 | 1.E−02M DMSO | 1.E−04M H2O |
| | | | | 5.E−02M DMSO* | Direct addition * |
| 9327-6 | AdPhAE/C6 | compound 6 | 376.00 | 1.E−02M DMSO | 1.E−04M H2O |
| 9327-7 | Al142Me/C8 | compound 8 | 332.00 | 1.E−02M DMSO | 1.E−04M H2O |
| 9327-8 | Ad2PhPZMe/C3 | compound 3 | 437.00 | 1.E−02M DMSO | 1.E−04M H2O |
| 9327-9 | AdPh3/VC7 | compound VC7 | 374.00 | 1.E−02M DMSO | 1.E−04M H2O |

F.W.: Formula Weight
* : for the isolated organ bioassay

Results

1.4. In Vitro Pharmacology: Binding Assays

The mean values for the effects of the test compounds are summarized in table 1-1.

The individual data obtained with the test compounds are reported in table 1-2.

The $IC_{50}$ and $K_i$ values for each reference compound are indicated in table 1-3. Each is within accepted limits of the historic average±0.5 log units.

1.5. Reference Compounds

In each experiment, the respective reference compound was tested concurrently with the test compounds in order to assess the assay suitability. It was tested at several concentrations and the data were compared with historical values. The assay was rendered valid if the suitability criteria were met, in accordance with the corresponding Standard Operating Procedure.

TABLE 1-1

Summary Results

| Assay Cerep Compound I.D. | Client Compound I.D. | Test Concentration (M) | % Inhibition of Control Specific Binding |
|---|---|---|---|
| \multicolumn{4}{c}{$\sigma_1$ (h)} |
| 9327-1 | (+) A1-41 | 1.0E−06 | 66 |
| 9327-2 | (−) A1-41 | 1.0E−06 | 65 |
| 9327-3 | (+) A2-73 | 1.0E−06 | 19 |
| 9327-4 | (−) A2-73 | 1.0E−06 | 50 |
| 9327-6 | AdPhAE/C6 | 1.0E−06 | 97 |
| 9327-7 | Al142Me/C8 | 1.0E−06 | 63 |
| 9327-8 | Ad2PhPZMe/C3 | 1.0E−06 | 81 |
| 9327-8 | Ad2PhPZMe/C3 | 1.0E−05 | 95 |
| 9327-9 | AdPh3/VC7 | 1.0E−06 | 95 |
| 9327-9 | AdPh3/VC7 | 1.0E−05 | 102 |
| \multicolumn{4}{c}{$\sigma_2$} |
| 9327-1 | (+) A1-14 | 1.0E−06 | 42 |
| 9327-2 | (−) A1-14 | 1.0E−06 | 59 |
| 9327-3 | (+) A2-73 | 1.0E−06 | 14 |
| 9327-4 | (−) A2-73 | 1.0E−06 | −13 |
| 9327-6 | AdPhAE/C6 | 1.0E−06 | 78 |
| 9327-7 | Al142Me/C8 | 1.0E−06 | 17 |
| 9327-8 | Ad2PhPZMe/C3 | 1.0E−06 | −9 |
| 9327-8 | Ad2PhPZMe/C3 | 1.0E−05 | 57 |
| 9327-9 | AdPh3/VC7 | 1.0E−06 | 84 |
| 9327-9 | AdPh3/VC7 | 1.0E−05 | 106 |

TABLE 1-2

Individual Data

| Assay Cerep Compound I.D. | Client Compound I.D. | Test Concentration (M) | % of Control Specific Binding 1st | 2nd | Mean |
|---|---|---|---|---|---|
| \multicolumn{6}{c}{$\sigma_1$ (h)} |
| 9327-1 | (+) A1-41 | 1.0E−06 | 35.0 | 32.9 | 34.0 |
| 9327-2 | (−) A1-41 | 1.0E−06 | 35.7 | 33.3 | 34.5 |
| 9327-3 | (+) A2-73 | 1.0E−06 | 81.5 | 81.1 | 81.3 |
| 9327-4 | (−) A2-73 | 1.0E−06 | 50.7 | 50.0 | 50.4 |
| 9327-6 | AdPhAE/C6 | 1.0E−06 | 4.3 | 1.9 | 3.1 |
| 9327-7 | Al142Me/C8 | 1.0E−06 | 46.2 | 28.1 | 37.1 |
| 9327-8 | Ad2PhPZMe/C3 | 1.0E−06 | 22.1 | 15.1 | 18.6 |
| 9327-8 | Ad2PhPZMe/C3 | 1.0E−05 | 5.0 | 5.7 | 5.4 |
| 9327-9 | AdPh3/VC7 | 1.0E−06 | 7.5 | 2.6 | 5.0 |
| 9327-9 | AdPh3/VC7 | 1.0E−05 | −4.4 | 0.8 | −1.8 |
| \multicolumn{6}{c}{$\sigma_2$} |
| 9327-1 | (+) A1-41 | 1.0E−06 | 60.0 | 56.8 | 58.4 |
| 9327-2 | (−) A1-41 | 1.0E−06 | 41.0 | 40.3 | 40.7 |
| 9327-3 | (+) A2-73 | 1.0E−06 | 88.9 | 83.2 | 86.1 |
| 9327-4 | (−) A2-73 | 1.0E−06 | 126.1 | 100.6 | 113.4 |
| 9327-6 | AdPhAE/C6 | 1.0E−06 | 19.6 | 24.6 | 22.1 |
| 9327-7 | Al142Me/C8 | 1.0E−06 | 84.0 | 81.0 | 82.5 |
| 9327-8 | Ad2PhPZMe/C3 | 1.0E−06 | 103.7 | 113.9 | 108.8 |
| 9327-8 | Ad2PhPZMe/C3 | 1.0E−05 | 45.2 | 40.5 | 42.9 |
| 9327-9 | AdPh3/VC7 | 1.0E−06 | 1.6 | 30.2 | 15.9 |
| 9327-9 | AdPh3/VC7 | 1.0E−05 | −11.1 | −0.2 | −5.7 |

TABLE 1-3

Reference Compound Data

| Assay Reference Compound | IC$_{50}$ (M) | K$_i$ (M) | n$_H$ |
|---|---|---|---|
| σ$_1$ (h) | | | |
| haloperidol | 1.3E-08 | 1.1E-08 | 0.8 |
| σ$_2$ | | | |
| haloperidol | 1.5E-07 | 1.3E-07 | 1.1 |
| haloperidol | 1.0E-07 | 8.6E-08 | 0.6 |

1.6. In Vitro Pharmacology: Isolated Organ Bioassay

The effects of (+) A1-41, (−) A1-41 and (−) A2-73 investigated for agonist and antagonist activities at the muscarinic M$_1$ receptors in the rabbit vas deferens are presented in table 2-1 where those of the reference compounds are also reported.

In the field-stimulated rabbit vas deferens, the M$_1$ receptor agonist McN-A-343 induced a concentration-dependent decrease in the twitch contraction amplitude which was reversed by the antagonist pirenzepine in a concentration-dependent manner.

In the untreated tissues, (+) A1-41, (−) A1-41 and (−) A2-73 did not decrease the twitch contraction amplitude but caused a slight to moderate increase.

In the tissues previously depressed with McN-A-343, (+) A1-41, (−) A1-41 and (−) A2-73 produced a concentration-dependent and almost complete recovery of the twitch contraction amplitude.

These results indicate that (+) A1-41, (−) A1-41 and (−) A2-73 behave as antagonists at the M$_1$ receptors.

TABLE 2-1

Effects of (+) AE 14, (−) AE 14 and (−) AE 37 investigated for agonist and antagonist activities at the muscarinic M$_1$ receptors in the rabbit vas deferens Test for agonist activity

| Compounds | Control response to McN-A-343 (1.0E-06M) | Responses to increasing concentrations of the compounds | | | + pirenzepine (1.0E-07M) |
|---|---|---|---|---|---|
| | | 1.0E-06M | 1.0E-05M | 5.0E-05M | |
| (+) AE 14 | 100 | −16 | −31 | | not tested |
| (−) AE 14 | 100 | −5 | −8 | | not tested |
| (−) AE 37 | 100 | | −20 | −33 | not tested |
| | | 1.0E-07M | 3.0E-07M | 1.0E-06M | |
| McN-A-343 | 100 | 29 | 67 | 99 | −5 |

Test for antagonist activity

| Compounds | Control response to McN-A-343 (1.0E-06M) | Responses to McN-A-343 (1.0E-06M) in the presence of increasing concentrations of the compounds | | |
|---|---|---|---|---|
| | | 1.0E-06M | 1.0E-05M | 5.0E-05M |
| (+) AE 14 | 100 | 13 | 1 | |
| (−) AE 14 | 100 | 20 | 9 | |
| (−) AE 37 | 100 | | 16 | −1 |

TABLE 2-1-continued

Effects of (+) AE 14, (−) AE 14 and (−) AE 37 investigated for agonist and antagonist activities at the muscarinic M$_1$ receptors in the rabbit vas deferens

| | 1.0E-08M | 3.0E-08M | 1.0E-07M |
|---|---|---|---|
| pirenzepine | 100 | 72 | 43 | 4 |

The results are expressed as a percent of the control response to McN-A-343 (decrease in twitch contraction amplitude) (mean values; n=2)

Example 1

Neuroprotection Against Beta Amyloid

A 67 year old male diagnosed with early stage Alzheimer's dementia is treated with 10 mg of ⊖Anevex2-73 substantially free of Anavex2-73⊕, once per week for three years. His mental function is tested quarterly and does not decrease over the period. On autopsy, his brain is found to contain senile plaques but very low content in amyloid peptide oligomers.

Example 2

Neuroprotection Against Oxidative Stress

A 29 year old female balloonist, anticipating anoxic stress, is orally administered 10 mgs of oral ⊖Anevex2-73 substantially free of Anavex2-73 ⊕ daily for 5 days preceding a balloon ascent. The balloonist ascends to 6,000 meters without oxygen assist and suffers no anoxic damage.

Example 3

Neuroprotection Against Neurotoxicity

A 37 year old male hazardous materials engineer, anticipating neurotoxic stress ⊕ is orally administered 1 mg of ⊖ Anevex2-73 substantially free of Anavex2-73⊕, daily for 5 days preceding exposure to tetanus toxin. The engineer is exposed 0.1 ng/kg of said neurotoxin and suffers no damage.

Example 4

Neuroprotection in Stroke Patient

A 57 year old male enters the emergency room and is diagnosed with an ischemic event involving the middle cerebral artery, with symptomatology onset being less than 1 hr. Immediately, the patient is administered an i.v. supplemented with 1 mg of ⊖Anevex2-73 substantially free of Anavex2-73⊕ while blood supply to the restricted area is restored. Daily testing of cognitive and motor systems show no deficits in physical or mental capacities. In addition, CT/MRI imaging shows no signs of lesioning in the affected region, immediately following recovery and that this was maintained and confirmed by follow-up imaging and behavior testing.

Example 5

Neuroprotection Against Amyloid

An 80 year old female patient is diagnosed with AD and treated with 10 mg of ⊖Anevex2-73 substantially free of Anavex2-73⊕ daily for 3 yrs. The patient's cognitive score stabilizes and then increases slowly and regularly over the following months.

Dosing Information/Dosage Forms:

For ⊖Anevex2-73 substantially free of Anavex2-73 ⊕ dosages of about 0.01-100 mg/daily, preferably 0.5-10 mg/daily, more preferably 0.5-2 mg/daily are noted. Dosing once every two days (3 times a week) is noted. AD is a chronic disease, so staring treatment promptly with diagnosis is preferred.

Particular attention is drawn to the method of this invention comprising ⊖ Anevex2-73 substantially free of Anavex2-73⊕ administration. In some instances therapeutic treatment includes administration of at least one cooperating acetylcholinesterase inhibitor (donepezil, galantamine, rivastigmine, or memantine), wherein at least one of said therapeutically effective amounts of either or the dose of cooperating acetylcholinesterase inhibitor is sub-therapeutic (sub-MAD) as compared to the active dose when used alone. Either the ⊖Anevex2-73 substantially free of Anavex2-73⊕ or the cooperating acetylcholinesterase inhibitor is used. In this regard, reference is made to U.S. Ser. No. 13/940,352 to Vamvakides et al entitled "ANAVEX2-73 AND CERTAIN ANTICHOLINESTERASE INHIBITORS COMPOSITION AND METHOD FOR NEUROPROTECTION" the teachings of which are incorporated herein by reference.

The compositions of this invention individually or in combination are employed in admixture with conventional excipients, i.e., pharmaceutically acceptable organic or inorganic carrier substances suitable for parenteral, enteral (e.g., oral or inhalation) or topical application which do not deleteriously react with the active compositions. Suitable pharmaceutically acceptable carriers include but are not limited to water, salt solutions, alcohols, gum arabic, vegetable oils, benzyl alcohols, polyethylene glycols, gelatin, carbohydrates such as lactose, amylose or starch, magnesium stearate, talc, titanium dioxide, silicic acid, viscous paraffin, perfume oil, fatty acid esters, hydroxy methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compositions. They can also be combined where desired with other active agents, e.g., vitamins.

In some embodiments of the present invention, dosage forms include instructions for the use of such compositions.

For parenteral application, particularly suitable are injectable, sterile solutions, preferably oily or aqueous solutions, as well as suspensions, emulsions, or implants, including suppositories. Ampules, vials, and injector cartridges are convenient unit dosages.

"Unit dosage form" shall mean single drug administration entity. By way of example, a single tablet, capsule, dragee, or trochee, suppository, or syringe.

Also for parenteral application, particularly suitable are tablets, dragees, liquids, drops, suppositories, or capsules. A syrup, elixir, or the like can be used wherein a sweetened vehicle is employed. Sublingual and buccal forms are also noted.

Sustained or directed release compositions can be formulated, e.g., liposomes or those wherein the active component is protected with differentially degradable coatings, e.g., by microencapsulation, multiple coatings, etc. It is also possible to freeze-dry the new compositions and use the lyophilizates obtained, for example, for the preparation of products for injection.

The invention claimed is:

1. A method of determining a therapeutic effect of a sigma 1 therapy in a subject, comprises the steps of:
   (i) collecting a first cell population from the subject at a first time point;
   (ii) exposing the first cell population to a composition of enantiomer (−) tetrahydro-N,N-dimethyl-2,2-diphenyl-3-furanmethanamine hydrochloride ((−) A2-73);
   (iii) determining a first level of cell binding at the first time point by measuring the specific binding of the composition to the first cell population using a competitive binding assay and a competing constitutively binding ligand;
   (iv) repeating step (ii) in a fixed cadent for a period of time, and obtain a post-treated cell population;
   (v) exposing the post-treated cell population to the same amount of the same composition as exposed to the first cell population;
   (vi) determining a post-treated cell binding from the post-treated cell population by measuring the specific binding of (−) A2-73 to the post-treated cell population using the competitive binding assay and the competing constitutively binding ligand; and
   (v) comparing the post-treated cell binding with the first level of cell binding;
   determining there is a positive therapeutic effect of the sigma 1 therapy, if the post-treated cell binding is higher than the first level of cell binding; or
   determining there is a negative therapeutic effect of the sigma 1 therapy, if the post-treated cell binding is lower than the first level of cell binding.

2. The method of claim 1, wherein the subject is a subject having or is suspect of having a neurological disorder.

3. The method of claim 1, wherein the composition of enantiomer (−) A2-73 is substantially free of (+) A2-73.

4. The method of claim 1, wherein the composition of enantiomer of the (−) A2-73 comprises from about 0.5 mg to about 100 mg of (−) A2-73.

* * * * *